(12) United States Patent
Luo et al.

(10) Patent No.: US 7,223,544 B2
(45) Date of Patent: May 29, 2007

(54) NUCLEIC ACID-ENGINEERED MATERIALS

(75) Inventors: Dan Luo, Ithaca, NY (US); Yougen Li, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/877,697

(22) Filed: Jun. 25, 2004

(65) Prior Publication Data

US 2005/0130180 A1  Jun. 16, 2005

Related U.S. Application Data

(60) Provisional application No. 60/483,032, filed on Jun. 27, 2003.

(51) Int. Cl.
*C12Q 1/68* (2006.01)
*C07H 21/02* (2006.01)
*C07H 21/04* (2006.01)

(52) U.S. Cl. .................. 435/6; 435/91.52; 536/23.1; 536/24.2

(58) Field of Classification Search .................. None
See application file for complete search history.

(56) References Cited

U.S. PATENT DOCUMENTS

| | | | |
|---|---|---|---|
| 6,197,556 B1 * | 3/2001 | Ulanovsky et al. | 435/91.2 |
| 2003/0036065 A1 * | 2/2003 | Gellibolian | 435/6 |
| 2005/0112578 A1 * | 5/2005 | Matsuura et al. | 435/6 |

OTHER PUBLICATIONS

Ma et al. ("Three-arm nucleic acid junctions are flexible" Nucleic Acids Research. 1986. vol. 14, No. 24: pp. 9745-9753).*
Seeman ("The use of branched DNA for nanoscale fabrication" Nanotechnology. 1991. 2: pp. 149-159).*
Kadramas et al. ("Relative stabilites of DNA three-way, four-way, and five-way junctions (multi-helix junction loops): unpaired nucleotides can be stabilizing or destabilizing" Nucleic Acids Research. 1995. vol. 23, No. 12: pp. 2212-2222).*
http://dictionary.reference.com/search?q=isotropic.*
Ma et al. "Three-arm nucleic acid junctions are flexible" Nucleic Acids Res. Dec. 22, 1986;14(24);9745-53.*
Seeman "The Use of Branched DNA for Nanoscale Fabrication" Nanotechnology 2:149-159 (1992).*
Seeman "Construction of three-dimensional stick figures from branched DNA" DNA Cell Biol. Sep. 1991;10(7):475-86.*
Alderman, L.M., "Molecular Computation of Solutions to Combinatorial Problems," *Science* 266:1021-1024 (1994).
Alivisatos et al., "Organization of 'Nanocrystal Molecules' Using DNA," *Nature* 382:609-611 (1996).
Altschul et al., "Basic Local Alignment Search Tool," *J. Mol. Biol.* 215:403-410 (1990).

(Continued)

*Primary Examiner*—Kenneth R. Horlick
*Assistant Examiner*—Christopher M. Babic
(74) *Attorney, Agent, or Firm*—Wilson Sonsini Goodrich & Rosati

(57) ABSTRACT

The present invention relates to the design and use of nucleic acid molecules to create novel materials. The present invention further relates to the use of DNA as a bulding block for DNA-materials that are of high yield and purity and that can be incorporated into larger structures.

14 Claims, 9 Drawing Sheets

OTHER PUBLICATIONS

Altschul et al., "Gapped BLAST and PSI-BLAST: A New Generation of Protein Database Search Programs," *Nucleic Acids Res.* 25(17):3389-3402 (1997).
Benenson et al., "Programmable and Autonomous Computing Machine Made of Biomolecules," *Nature* 414;430-434 (2001).
Bouchiat et al., "Estimating the Persistence Length of a Worm-Like Chain Molecule from Force-Extension Measurements," *Biophys. J.* 76:409-413 (1999).
Braun et al, "DNA-Templated Assembly and Electrode Attachment of a Conducting Silver Wire," *Nature* 391:775-778 (1998).
Corpet, F., "Multiple Sequence Alignment with Hierarchical Clustering," *Nucleic Acids Res.* 16(22):10881-10890 (1988).
Demers et al., "Direct Patterning of Modified Oligonucleotides on Metals and Insulators by Dip-Pen Nanolithography," *Science* 296:1836-1838 (2002).
Drexler, K.E., "Molecular Engineering: An Approach to the Development of General Capabilities for Molecular Manipulation," *Proc. Natl. Acad. Sci. USA* 78(9):5275-5278 (1981).
Eckardt et al., "Chemical Copying of Connectivity," *Nature* 420:286 (2002).
Elghanian et al., "Selective Colorimetric Detection of Polynucleotides Based on the Distance-Dependent Optical Properties of Gold Nanoparticles," *Science* 277:1078-1081 (1997).
Feynman, R.P., "There's Plenty of Room at the Bottom," in *Miniaturization*, Horace D. Gilbert Ed., Reinhold Publishing Corporation, New York, pp. 282-296 (1961).
Guarnieri et al., "Making DNA Add," *Science* 273:220-223 (1996).
Higgins et al., "CLUSTAL: A Package for Performing Multiple Sequence Alignment on a Microcomputer," *Gene* 73:237-244 (1988).
Higgins et al., "Fast and Sensitive Multiple Sequence Alignments on a Microcomputer," *CABIOS Commun.* 5(2):151-153 (1989).
Huang et al., "Parallelization of a Local Similarity Algorithm," *CABIOS* 8(2):155-165 (1992).
Kallenbach et al., "Fourth Rank Immobile Nucleic Acid Junctions," *J. Biomol. Struct. Dyn.* 1:159-168 (1983).
Karlin et al., "Applications and Statistics for Multiple High-Scoring Segments in Molecular Sequences," *Proc. Natl. Acad. Sci. USA* 90:5873-5877 (1993).
Karlin et al., "Methods for Assessing the Statistical Significance of Molecular Sequence Features by Using General Scoring Schemes," *Proc. Natl. Acad. Sci. USA* 87:2264-2268 (1990).
Keren et al., "Sequence-Specific Molecular Lithography on Single DNA Molecules," *Science* 297:72-75 (2002).
LaBean et al., "Construction, Analysis, Ligation, and Self-Assembly of DNA Triple Crossover Complexes," *J. Am. Chem. Soc.* 122:1848-1860 (2000).
Luo, D., "Novel Crosslinking Technologies to Assess Protein-DNA Binding and DNA-DNA Complexes for Gene Delivery and Expression," Molecular, Cellular, and Developmental Biology Program, The Ohio State University (1997) (Dissertation).
Ma et al., "Three-Arm Nucleic Acid Junctions are Flexible," *Nucleic Acids Res.* 14(24):9745-9753 (1986).
Mao et al., "A Nanomechanical Device Based on the B-Z Transition of DNA," *Nature* 397:144-146 (1999).
Mao et al., "Assembly of Borromean Rings from DNA," *Nature* 386:137-138 (1997).
Mao et al., "Designed Two-Dimensional DNA Holliday Junction Arrays Visualized by Atomic Force Microscopy," *J. Am. Chem. Soc.* 121:5437-5443 (1999).
Mao et al., "Logical Computation Using Algorithmic Self-Assembly of DNA Triple-Crossover Molecules," *Nature* 407:493-496 (2000).
Mirkin et al., "A DNA-Based Method for Rationally Assembling Nanoparticles Into Macroscopic Materials," *Nature* 382:607-609 (1996).
Myers et al., "Optimal Alignment in Linear Space," *CABIOS* 4(1):11-17 (1988).
Needleman et al., "A General Method Applicable to the Search for Similarities in the Amino Acid Sequence of Two Proteins," *J. Mol. Biol.* 48:443-453 (1970).
Niemeyer et al., "Covalent DNA—Streptavidin Conjugates as Building Blocks for Novel Biometallic Nanostructures, " *Angew. Chem. Int. Ed.* 37 (16):2265-2268 (1998).
Niemeyer, C.M., "Nanoparticles, Proteins, and Nucleic Acids: Biotechnology Meets Materials Science," *Angew. Chem. Int. Ed.* 40:4129-4158 (2001).
Niemeyer, C.M., "Progress in "Engineering Up" Nanotechnology Devices Utilizing DNA as a Construction Material," *Appl. Phys. A* 68:119-124 (1999).
Nilsen et al., "Dendritic Nucleic Acid Structures," *J. Theor. Biol.* 187:273-284 (1997).
Ouyang et al., "DNA Solution of the Maximal Clique Problem," *Science* 278:446-449 (1997).
Park et al., "Array-Based Electrical Detection of DNA with Nanoparticle Probes," *Science* 295:1503-1506 (2002).
Pearson et al., "Improved Tools for Biological Sequence Comparison," *Proc. Natl. Acad. Sci. USA* 85:2444-2448 (1988).
Pearson, W.R., "Using the FASTA Program to Search Protein and DNA Sequence Databases," *Meth. Mol. Biol.*, 24:307-331 (1994).
Robinson et al., "The Design of a Biochip: A Self-Assembling Molecular-Scale Memory Device," *Prot. Eng.* 1(4):295-300 (1987).
Sakamoto et al., "Molecular Computation by DNA Hairpin Formation," *Science* 288:1223-1226 (2000).
Seeman et al., "Designed Two Dimensional Holliday Junction Arrays," *Biophys. J.* 78:308a (2000) (abstract).
Seeman et al., "Emulating Biology: Building Nanostructures from the Bottom Up," *Proc. Natl. Acad. Sci. USA* 99(Suppl. 2):6451-6455 (2002).
Seeman, N.C., "Construction of Three-Dimensional Stick Figures from Branched DNA," *DNA & Cell Biol.* 10(7):475-486 (1991).
Seeman, N.C., "*De Novo* Design of Sequences for Nucleic Acid Structural Engineering," *J. Biomol. Struct. Dyn.* 8(3):573-581 (1990).
Seeman, N.C., "DNA Components for Molecular Architecture," *Acc. Chem. Res.* 30:357-363 (1997).
Seeman, N.C., "DNA Engineering and Its Application to Nanotechnology," *Trends in Biotech.* 17:437-443 (1999).
Seeman, N.C., "DNA Nanotechnology: Novel DNA Constructions," *Annu. Rev. Biophys. Biomol. Struct.* 27:225-248 (1998).
Seeman, N.C., "The Use of Branched DNA for Nanoscale Fabrication," *Nanotechnology* 2:149-159 (1991).
Sha et al., "Atomic Force Microscopy of Parallel DNA Branched Junction Arrays," *Chemistry & Biology* 7:743-751 (2000).
Smith et al., "Comparison of Biosequences," *Adv. Appl. Math.* 2:482-489 (1981).
Smith et al., "Direct Mechanical Measurements of the Elasticity of Single DNA Molecules by Using Magnetic Beads," *Science* 258:1122-1126 (1992).
Taton et al., "The DNA-Mediated Formation of Supramolecular Mono- and Multilayered Nanoparticle Structures," *J. Am. Chem. Soc.* 122:6305-6306 (2000).
Tijssen, P., "Overview of Principles of Hybridization and the Strategy of Nucleic Acid Probe Assays," in *Laboratory Techniques in Biochemistry and Molecular Biology*, Part 1, Chapter 2, Hybridization with Nucleic Acid Probes, Elsevier, New York, pp. 20-78 (1993).
Tinland et al., "Persistence Length of Single-Stranded DNA," *Macromolecules* 30:5763-5765 (1997).
Tóth et al., "DNA Curvature in Solution Measured by Fluorescence Resonance Energy Transfer," *Biochemistry* 37:8173-8179 (1998).
Wang et al., "Dendritic Nucleic Acid Probes for DNA Biosensors," *J. Am. Chem. Soc.* 120:8281-8282 (1998).
Watson et al., "DNA-Block Copolymer Conjugates," *J. Am. Chem. Soc.* 123:5592-5593 (2001).
Winfree et al., "Design and Self-Assembly of Two-Dimensional DNA Crystals," *Nature* 394:539-544 (1998).
Yan et al., "A Robust DNA Mechanical Device Controlled by Hybridization Topology," *Nature* 415:62-65 (2002).
Yang et al., "Ligation of DNA Triangles Containing Double Crossover Molecules," *J. Am. Chem. Soc.* 120:9779-9786 (1998).
Dadlani, M. N. Image processing of DNA nanobarcode. The Graduate School of Cornell University (2005) (Dissertation).
Li, et al. Controlled Assembly of Dendrimer-like DNA. Nature Materials. 2004; 3:38-42.

* cited by examiner

FIG. 3A

AGCTAGAGGTGCGATTG TACCAGCGTTCA
CAATCGACTCT ATGGTCGCAAGTCCTAG

GTCATGCTACTGTGTCT
ACGATGACAGA

FIG. 8

NUCLEIC ACID-ENGINEERED MATERIALS

This application claims the benefit of U.S. Provisional Patent Application Ser. No. 60/483,032, filed Jun. 27, 2003.

The invention was made, at least in part, with the support of a grant from the Government of the United States of America (grant ECS-9731293 from the National Science Foundation, which supports the Cornell Nanofabrication Facility). The Government may have certain rights to the invention.

FIELD OF THE INVENTION

The present invention relates to the use of nucleic acid molecules to create novel materials.

BACKGROUND OF THE INVENTION

A key aim of biotechnology and nanotechnology is the construction of new biomaterials, including individual geometrical objects, nanomechanical devices, and extended constructions that permit the fabrication of intricate structures of materials to serve many practical purposes (Feynman et al., *Miniaturization* 282–296 (1961); Drexler, *Proc. Nat. Acad. Sci. (USA)* 78:5275–5278 (1981); Robinson et al., *Prot Eng* 1 295–300 (1987); Seeman, *DNA & Cell Biol.* 10:475–486 (1991); Seeman, *Nanotechnol* 2:149–159 (1991)). Molecules of biological systems, for example, nucleic acids, have the potential to serve as building blocks for these constructions due to their self and programmable-assembly capabilities.

DNA molecules possess a distinct set of mechanical, physical, and chemical properties. From a mechanical point of view, DNA molecules can be rigid (e.g., when the molecules are less than 50 nm, the persistent length of double stranded DNA (Bouchiat, C. et al., *Biophys J* 76:409–13 (1999); Tinland et al., *Macromolecules* 30:5763–5765 (1997); Toth et al., *Biochemistry* 37:8173–9 (1998)), or flexible. Physically, DNA is small, with a width of about 2 nanometers and a length of about 0.34 nanometers per basepair (for B-DNA). In nature, DNA can be found in either linear or circular shapes. Chemically, DNA is generally stable, non-toxic, water soluble, and is commercially available in large quantities and in high purity. Moreover, DNA molecules are easily and highly manipulable by various well-known enzymes such as restriction enzymes and ligases. Also, under proper conditions, DNA molecules will self-assemble with complementary strands of nucleic acid (e.g., DNA, RNA, or Peptide Nucleic Acid, (PNA)), proteins or peptides. Furthermore, DNA molecules can be amplified exponentially and ligated specifically. Thus, DNA is an excellent candidate for constructing nano-material.

The concept of using DNA molecules for non-genetic application has only recently emerged as two new fields of research: DNA-computation, such as using DNA as algorithms for solving combinatorial problems (Adleman, *Science* 266:1021–4 (1994); Guarnieri et al., *Science* 273:220–3 (1996); Ouyang et al., *Science* 278:446–9 (1997); Sakamoto et al., *Science* 288:1223–6 (2000); Benenson et al., *Nature* 414:430–4 (2001)), and DNA-nanotechnology, such as using DNA molecules for nano-scaled frameworks and scaffolds (Niemeyer, *Applied Physics a-Materials Science & Processing* 68:119–124 (1999); Seeman, *Annual Review of Biophysics and Biomolecular Structure* 27:225–248 (1998)). However, the design and production of DNA-based materials is still problematic (Mao et al., *Nature* 397:144–146 (1999); Seeman et al., *Proc Natl Acad Sci USA* 99:6451–6455 (2002); Yan et al., *Nature* 415:62–5 (2002); Mirkin et al., *Nature* 382:607–9 (1996); Watson et al., *J Am Chem Soc* 123:5592–3 (2001)). For example, previously reported nucleic acid structures were quite polydispersed with flexible arms and self-ligated circular and non-circular byproducts (Ma et al., *Nucleic Acids Res* 14:9745–53 (1986); Wang et al., *Journal of the American Chemical Society* 120:8281–8282 (1998); Nilsen et al., *J Theor Biol* 187:273–84 (1997)), which severely limited their utility in constructing DNA materials. The yield and purity of those structures were also unknown.

Alderman first solved an instance of the directed Hamiltonian path problem using DNA molecules and reactions (Adleman, *Science* 266:1021–4 (1994)). Since then, DNA has been used as algorithms for solving combinatorial problems (Guarnieri et al., *Science* 273:220–3 (1996); Ouyang et al., *Science* 278:446–9 (1997); Sakamoto et al., *Science* 288:1223–6 (2000); Benenson et al., *Nature* 414:430–4 (2001)) and logical computation (Mao et al., *Nature* 407:493–6 (2000)). However, in all of these applications, the shapes of DNA molecules have not been altered; they are still in linear form as the hair-pin form was employed, which is also a linear form.

The field of DNA nanotechnology was pioneered by Seeman (Seeman, *J Biomol Struct Dyn* 8:573–81 (1990); Seeman, *Accounts of Chemical Research* 30:357–363 (1997); Seeman, *Trends in Biotechnology* 17:437–443 (1999)). Using rigid "crossover" DNA as building blocks, motifs were constructed (Seeman et al., *Biophysical Journal* 78:308a–308a (2000); Sha et al., *Chemistry & Biology* 7:743–751 (2000); LaBean et al., *Journal of the American Chemical Society* 122:1848–1860 (2000); Yang et al., *Journal of the American Chemical Society* 120:9779–9786 (1998); Mao et al., *Nature* 386:137–138 (1997)). A DNA mechanical device was also reported (Mao et al., *Journal of the American Chemical Society* 121:5437–5443 (1999); Yan et al., *Nature* 415:62–5 (2002)). However, the building blocks and motifs employed so far are isotropic multivalent, possibly useful for growing nano-scaled arrays and scaffolds (Winfree et al., *Nature* 394:539–44 (1998); Niemeyer, *Applied Physics a-Materials Science & Processing* 68:119–124 (1999); Seeman, *Annual Review of Biophysics and Biomolecular Structure* 27:225–248 (1998)), but not suitable for controlled growth, such as in dendrimer, or in creating a large quantity of monodispersed new materials, which are important to realize nucleic acid-based materials.

Other schemes of nano-construction using linear DNA molecules were also reported, including a biotin-avidin based DNA network (Luo, "Novel Crosslinking Technologies to Assess Protein-DNA Binding and DNA-DNA Complexes for Gene Delivery and Expression" (Dissertation). Molecular, Cellular, and Developmental Biology Program, The Ohio State University (1997)), nanocrystals (Alivisatos et al., *Nature* 382:609–11 (1996)), DNA-protein nanocomplexes (Niemeyer et al., *Angewandte Chemie-International Edition* 37:2265–2268 (1998)), a DNA-fueled molecular machine (Yurke et al., *Nature* 406:605–8 (2000)), DNA-block copolymer conjugates (Watson et al., *J Am Chem Soc* 123:5592–3 (2001)), DNA-silver-wire (Braun et al., *Nature* 391:775–8 (1998)), and DNA-mediated supramolecular structures (Taton et al., *Journal of the American Chemical Society* 122:6305–6306 (2000)). In addition, Mirkin has reported DNA sensing via gold nanoparticles (Elghanian et al., *Science* 277:1078–81 (1997)) and DNA patterning via dip-pen nanolithography (Demers et al., *Science* 296:1836–8 (2002)), although such patterning is not suitable for large scale production. Recently Mirkin's group reported a DNA array-based detection method that utilized microelectrodes, opening up possibilities for DNA-nanowires (Park et al., *Science* 295:1503–1506 (2002)). DNA-based lithography was recently reported by Braun's group where linear and very long DNA molecules were reported to serve as masks and RecA proteins served as resists (Keren et al., *Science* 297:72–5 (2002)). Recently, a small chemical, trislinker, was reportedly reacted with 5'-hydrazide-modified oligonucleotides in the presence of the 3'-tris-oligonucleotidyl template to allegedly create tri-valent, Y-shape DNA molecules (Eckardt et al., *Nature* 420:286 (2002)). However, all of these examples involved linear DNA.

Therefore, there is a need for nucleic acid-based materials and for methods to construct these materials.

SUMMARY OF THE INVENTION

The present invention provides a trimer, including a first, a second, and a third polynucleotide, where at least a portion of the first polynucleotide is complementary to at least a portion of the second polynucleotide, where at least a portion of the first polynucleotide is complementary to at least a portion of the third polynucleotide, where at least a portion of the second polynucleotide is complementary to at least a portion of the third polynucleotide, and where the first, second, and third polynucleotides are associated together to form a trimer.

The present invention further provides a nucleic acid assembly, including at least two of the trimers of associated together.

The present invention also provides a method of making a nucleic acid assembly by associating at least two trimers together.

The present invention also provides a method of making a trimer, including combining a first, a second, and a third polynucleotide in a solution, where at least a portion of the first polynucleotide is complementary to at least a portion of the second polynucleotide, where at least a portion of the first polynucleotide is complementary to at least a portion of the third polynucleotide, and where at least a portion of the second polynucleotide is complementary to at least a portion of the third polynucleotide. The solution is maintained at conditions effective for the first, second, and third polynucleotides to associate together to form a trimer.

There is currently a need for nucleic acid-based materials and for methods to construct such materials. To use DNA as a building block for DNA-materials, it is desirable to create different shapes of DNA molecules in high yield, high purity, and with the ability to be incorporated into larger structures. Therefore, branched DNA molecules (Y-shaped DNA) with precisely controlled size were constructed at nanoscale with high yield and purity. Using these simple and robust nanoscale building blocks, a stepwise synthesis scheme that successfully assembled the Y-DNA into dendrimer-like DNA (DL-DNA) nanoparticles was devised. The assembly of DL-DNA was precisely controlled at each step of growth, thus making it possible to synthesize monodisperse DNA nanoparticles of the same, or nearly the same, molecular weight. The DL-DNA finds its utility in numerous applications in both biomedical (e.g., controlled drug delivery, multi-function DNA carrier; DNA delivery) and non-biomedical fields (e.g., nanowire, DNA patterning).

This procedure, based on using Y-DNA as building blocks, is simple and robust. For example, the $4^{th}$ generation of DL-DNA is close to being monodisperse, even without purification. In addition, both the Y-DNA and the DL-DNA nanoparticles are very stable. Furthermore, no self-ligated products were detected, which was commonly seen in other types of design (Ma et al., *Nucleic Acids Res* 14:9745–53 (1986), which is hereby incorporated by reference in its entirety). This key improvement was due to the unique design of end sequences. Thus, specifically designed polynucleotides can be combined to form Y-DNA, and specific combinations of Y-DNAs can be combined to construct DL-DNA. Both Y-DNA and DL-DNA may be 3-dimensional, and may contain branches.

BRIEF DESCRIPTION OF THE FIGURES

FIG. 1 is a schematic drawing of DNA molecular assembly.

Figure 3A:
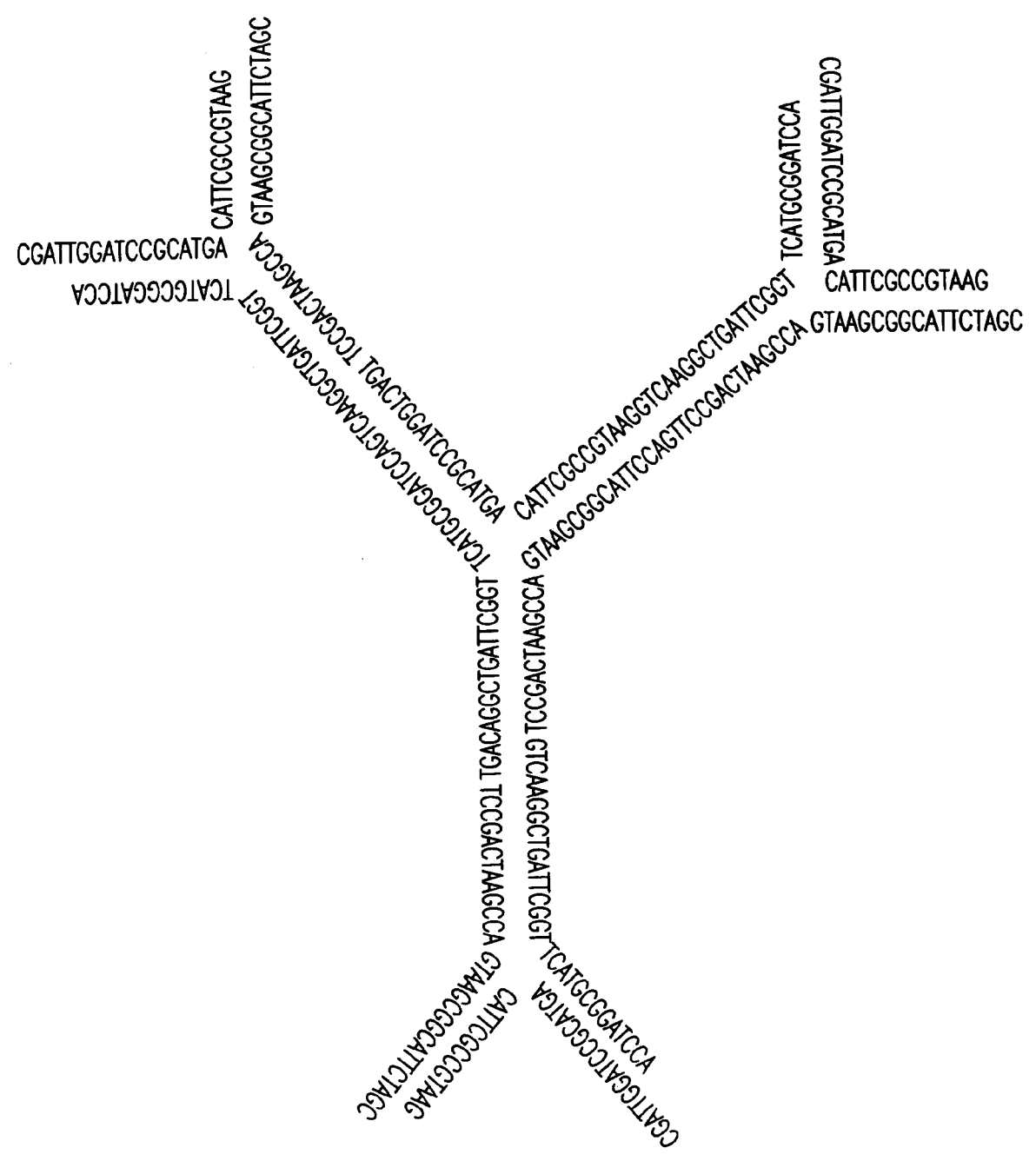

FIG. 3 depicts the characterization of the first generation dendrimer-like DNA ($G_1$). FIG. 3A depicts an example of sequences of $G_1$ DL-DNA.

FIG. 8 depicts a trimer in accordance with the present invention.

DETAILED DESCRIPTION OF THE INVENTION

Figure 1A:
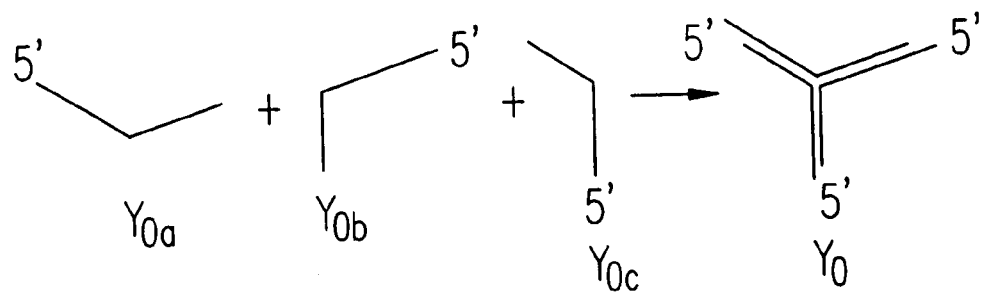
FIG. 1A depicts the assembly of Y-DNA. Three oligonucleotides were annealed together to form one Y-shape DNA, a basic building block for dendrimer-like DNA ($Y_{0a}+Y_{0b}+Y_{0c} \to Y_0$; $Y_{1a}+Y_{1b}+Y_{1c} \to Y_1$; $Y_{2a}+Y_{2b}+Y_{2c} \to Y_2$; $Y_{3a}+Y_{3b}+Y_{3c} \to Y_3$; $Y_{4a}+Y_{4b}+Y_{4c} \to Y_4$).

The present invention provides a trimer, including a first, a second, and a third polynucleotide, where at least a portion of the first polynucleotide is complementary to at least a portion of the second polynucleotide, where at least a portion of the first polynucleotide is complementary to at least a portion of the third polynucleotide, where at least a portion of the second polynucleotide is complementary to at least a portion of the third polynucleotide, and where the first, second, and third polynucleotides are associated together to form a trimer.

In some embodiments, each polynucleotide includes a first region, a second region located 3' to the first region, and a third region located 3' to the second region, where the second region of the first polynucleotide includes a region complementary to the third region of the third polynucleotide, the third region of the first polynucleotide includes a region complementary to the second region of the second polynucleotide, and the third region of the second polynucleotide includes a region complementary to the second region of the third polynucleotide. In some embodiments, the trimer has three branches. In some embodiments, at least one of the polynucleotides includes a sticky end. In some embodiments, the first region of the first, second and third polynucleotides includes a sticky end. In some embodiments, the first, second, and third polynucleotides are DNA.

Other molecules that may be incorporated include: RNA, PNA (peptide nucleic acid), TNA (threose nucleic acids), and other polymers that are able to complex with nucleic acids in a sequence specific manner.

The present invention also provides a nucleic acid assembly, including at least two of the trimers associated together. In some embodiments, the trimers are ligated together. In some embodiments, the assembly is a honeycomb structure.

The present invention also provides a method of making a nucleic acid assembly by associating at least two of the trimers together. In some embodiments, the association step includes ligating the trimers together.

The present invention also provides a method of making a trimer, including: combining a first, a second, and a third polynucleotide in a solution, where at least a portion of the first polynucleotide is complementary to at least a portion of the second polynucleotide, where at least a portion of the first polynucleotide is complementary to at least a portion of the third polynucleotide, and where at least a portion of the second polynucleotide is complementary to at least a portion of the third polynucleotide. The solution is maintained at conditions effective for the first, second, and third polynucleotides to associate together to form a trimer.

In some embodiments, the combining step includes the steps of: combining the first polynucleotide with the second polynucleotide in a solution to form a mixture; and subsequently combining the third polynucleotide with the first and second polynucleotides in the solution. In some embodiments, each polynucleotide includes a first region, a second region located 3' to the first region, and a third region located 3' to the second region, wherein the second region of the first polynucleotide includes a region complementary to the third region of the third polynucleotide, the third region of the first polynucleotide includes a region complementary to the second region of the second polynucleotide, the third region of the second polynucleotide includes a region complementary to the second region of the third polynucleotide. In some embodiments, at least one of the polynucleotides includes a sticky end. In some embodiments, the first region of the first, second and third polynucleotides includes a sticky end. In some embodiments, the first, second, and third polynucleotides are DNA.

Polynucleotides

The first step in the synthesis of the Y-DNA and DL-DNA materials of the present invention is the design and synthesis of specific polynucleotides of the invention. The following principles were followed in order to design sequences for DL-DNA (see, e.g., N. C. Seeman, "De Novo Design of Sequences for Nucleic Acid Structure Engineering," *Journal of Biomolecular Structure and Dynamics* 8:573–581 (1990); N. C. Seeman, "DNA Nanotechnology: Novel DNA Constructions," *Annual Review of Biophysics and Biomolecular Structure* 27:225–248 (1998), which are hereby incorporated by reference in their entirety). First, the free energy (deltaG) was calculated for a sequence. In general, a lower free energy is desired. However, intermediate-low deltaG are also considered. Second, the secondary structure of the molecule is considered. In general, the least amount of secondary structure is desired. Third, it needs to be determined if the molecule would form a self-dimer, as it should not form a self-dimer. Fourth, the length is considered, which can vary depending on the design goals. The molecule should be long enough to form stable DNA structure. For Y-DNA, it should be more than 8 nucleotides (nt) long. Fifth, the helix geometry, should be considered. Half-turns should be considered as the quantum of DNA nanostucture. The length between two junctions should be 5*n bp, where n is 0, 1, 2, 3 etc. Next, the G/C content should be considered. In one embodiment, sequences are chosen that constitute about 50% G/C. Last, the symmetry of the molecule should be considered. Sequence symmetry of each arm should be avoided. For Y-DNA sequence design, all three oligonucleotides should be checked at the same time. In one example, 4 consecutive nucleotides were used as a unit in the checking process. For example, Target sequence: AGCTGAT Check 1: AGCT. Since no other AGCT sequence appears in that sequence, the first sequence symmetry check passes.

Check 2: GCTG. Since no other GCTG sequence appears in that sequence, the second sequence symmetry check passes.

Check 3: CTGA. Similarly, the third sequence symmetry check passes.

Check 4: TGAT. Similarly, the fourth sequence symmetry check passes.

Three specific polynucleotides are combined to form each Y-DNA. Each polynucleotide may include three regions (e.g., see Table 1). A first region (region 1) of each polynucleotide may include nucleotides that will form a 5' sticky end when a Y-DNA is formed. A "sticky end" is a single-stranded overhang portion of one of the polynucleotides. In some embodiments of the present invention, the sticky ends can be 1, 2, 3, 4, 5, 6, 7, 8, 9, or 10 nucleotides. In some embodiments, a polynucleotide may not have this sticky end. In general, a shorter sticky end will allow for less selectivity in binding. For example, a polynucleotide lacking a sticky end would have little to no selectivity. The sticky end in some embodiments is a four nucleotide sticky end. In some embodiments, the sticky end includes, or is, TGAC (SEQ ID NO:16), GTCA (SEQ ID NO:17), CGAT (SEQ ID NO:18), ATCG (SEQ ID NO:19), GCAT (SEQ ID NO:20), ATGC (SEQ ID NO:21), TTGC (SEQ ID NO:22), GCAA (SEQ ID NO:23), or GGAT (SEQ ID NO:24) (see e.g., Tables 1 and 2).

The second region (region 2) of each polynucleotide is complementary to the third region (region 3) of one of the other two polynucleotides that form the Y-DNA. The third region of each polynucleotide is complementary to the second region of the other of the other two polynucleotides of Y-DNA. For example, with reference to the sequences in Tables 1 and 2: region 2 of SEQ ID NOs 1–5, represented by SEQ ID NO:25, is complementary to region 3 of SEQ ID NOs 11–15, represented by SEQ ID NO:30, region 3 of SEQ ID NOs 1–5, represented by SEQ ID NO:26, is complementary to region 2 of SEQ ID NOs 6–10, represented by SEQ ID NO:27; and region 2 of SEQ ID NOs 11–15, represented by SEQ ID NO:29, is complementary to region 3 of SEQ ID NOs 6–10, represented by SEQ ID NO:28.

In some embodiments of the invention, the length of each of the regions can vary. For example, in some embodiments, the second and/or third regions are about 13 nucleotides each in length. In some embodiments, the lengths of the second and/or third regions maybe 7, 8, 9, 10, 11, 12, 13, 14, 15, 16, 17, 18, 19, or 20 nucleotides in length. In some embodiments of the invention, the second and/or third regions may be larger than 20 nucleotides in length, for example they may be about 25, 30, 35, 40, 45, or 50 nucleotides in length.

In one embodiment of the invention, each polynucleotide is 30 nucleotides in length, with the first region having 4 nucleotides, the second region having 13 nucleotides, and the third region also having 13 nucleotides. In some embodiments of the invention, the polynucleotides include, essentially include, or are, SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and/or SEQ ID NO:15.

TABLE 1

Sequences of Oligonucleotides

| Strand | SEQ ID NO: | Region 1 | Region 2 | Region 3 |
|---|---|---|---|---|
| $Y_{0a}$ | 1 | 5'-TGAC | TGGATCCGCATGA | CATTCGCCGTAAG-3' |
| $Y_{1a}$ | 2 | 5'-GTCA | TGGATCCGCATGA | CATTCGCCGTAAG-3' |
| $Y_{2a}$ | 3 | 5'-ATCG | TGGATCCGCATGA | CATTCGCCGTAAG-3' |
| $Y_{3a}$ | 4 | 5'-ATGC | TGGATCCGCATGA | CATTCGCCGTAAG-3' |
| $Y_{4a}$ | 5 | 5'-GCAA | TGGATCCGCATGA | CATTCGCCGTAAG-3' |
| $Y_{0b}$ | 6 | 5'-TGAC | CTTACGGCGAATG | ACCGAATCAGCCT-3' |
| $Y_{1b}$ | 7 | 5'-CGAT | CTTACGGCGAATG | ACCGAATCAGCCT-3' |
| $Y_{2b}$ | 8 | 5'-GCAT | CTTACGGCGAATG | ACCGAATCAGCCT-3' |
| $Y_{3b}$ | 9 | 5'-TTGC | CTTACGGCGAATG | ACCGAATCAGCCT-3' |
| $Y_{4b}$ | 10 | 5'-GGAT | CTTACGGCGAATG | ACCGAATCAGCCT-3' |
| $Y_{0c}$ | 11 | 5'-TGAC | AGGCTGATTCGGT | TCATGCGGATCCA-3' |
| $Y_{1c}$ | 12 | 5'-CGAT | AGGCTGATTCGGT | TCATGCGGATCCA-3' |
| $Y_{2c}$ | 13 | 5'-GCAT | AGGCTGATTCGGT | TCATGCGGATCCA-3' |
| $Y_{3c}$ | 14 | 5'-TTGC | AGGCTGATTCGGT | TCATGCGGATCCA-3' |
| $Y_{4c}$ | 15 | 5'-GGAT | AGGCTGATTCGGT | TCATGCGGATCCA-3' |

TABLE 2

Sequence Table

| SEQ ID NO | Sequence |
|---|---|
| 1 | 5'-TGACTGGATCCGCATGACATTCGCCGTAAG-3' |
| 2 | 5'-GTCATGGATCCGCATGACATTCGCCGTAAG-3' |
| 3 | 5'-ATCGTGGATCCGCATGACATTCGCCGTAAG-3' |
| 4 | 5'-ATGCTGGATCCGCATGACATTCGCCGTAAG-3' |
| 5 | 5'-GCAATGGATCCGCATGACATTCGCCGTAAG-3' |
| 6 | 5'-TGACCTTACGGCGAATGACCGAATCAGCCT-3' |
| 7 | 5'-CGATCTTACGGCGAATGACCGAATCAGCCT-3' |
| 8 | 5'-GCATCTTACGGCGAATGACCGAATCAGCCT-3' |
| 9 | 5'-TTGCCTTACGGCGAATGACCGAATCAGCCT-3' |
| 10 | 5'-GGATCTTACGGCGAATGACCGAATCAGCCT-3' |
| 11 | 5'-TGACAGGCTGATTCGGTTCATGCGGATCCA-3' |
| 12 | 5'-CGATAGGCTGATTCGGTTCATGCGGATCCA-3' |
| 13 | 5'-GCATAGGCTGATTCGGTTCATGCGGATCCA-3' |
| 14 | 5'-TTGCAGGCTGATTCGGTTCATGCGGATCCA-3' |
| 15 | 5'-GGATAGGCTGATTCGGTTCATGCGGATCCA-3' |
| 16 | 5'-TGAC-3' |
| 17 | 5'-GTCA-3' |
| 18 | 5'-CGAT-3' |
| 19 | 5'-ATCG-3' |
| 20 | 5'-GCAT-3' |
| 21 | 5'-ATGC-3' |
| 22 | 5'-TTGC-3' |
| 23 | 5'-GCAA-3' |
| 24 | 5'-GGAT-3' |
| 25 | 5'-TGGATCCGCATGA-3' |
| 26 | 5'-CATTCGCCGTAAG-3' |
| 27 | 5'-CTTACGGCGAATG-3' |
| 28 | 5'-ACCGAATCAGCCT-3' |
| 29 | 5'-AGGCTGATTCGGT-3' |
| 30 | 5'-TCATGCGGATCCA-3' |

The present invention thus provides isolated and/or purified polynucleic acid sequences, for example, sequences including SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ NO:9, SEQ ID NO:10, SEQ ID NO:11, SEQ ID NO:12, SEQ ID NO:13, SEQ NO:14, or SEQ ID NO:15. These sequences can be DNA sequences and can be made by methods well known in the art and are useful to prepare the Y-DNA and DL-DNA of the present invention.

Sequences of the present invention may also be RNA, PNA, or TNA sequences.

The present invention also provides compositions including combinations of polynucleotides including SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and/or SEQ ID NO:15.

The present invention is also directed to polynucleic acid sequences that include any one of the sequences of region 1 (SEQ ID NOs 16–24), any one of the sequences of region 2 (SEQ ID NOs 25, 27 or 29), and any one of the sequences of region 3 (SEQ ID NOs 26, 28, or 30). These polynucleotides can be designed to produce Y-DNA and DL-DNA according to the methods disclosed herein.

As used herein, the terms "isolated and/or purified" refer to in vitro preparation, isolation and/or purification of a nucleic acid molecule of the invention, so that it is not associated with in vivo substances, or is substantially purified from in vitro substances.

The following terms are used to describe the sequence relationships between two or more polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a segment of or the entirety of a specified sequence.

(b) As used herein, "comparison window" makes reference to a contiguous and specified segment of a polynucleotide sequence, wherein the polynucleotide sequence in the comparison window may include additions or deletions (i.e., gaps) compared to the reference sequence (which does not include additions or deletions) for optimal alignment of the two sequences. Generally, the comparison window is at least 5, 10, or 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty can be introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, CABIOS, 4:11 (1988), which is hereby incorporated by reference in its entirety; the local homology algorithm of Smith et al., Adv. Appl. Math., 2:482 (1981), which is hereby incorporated by reference in its entirety; the homology alignment algorithm of Needleman and Wunsch, JMB, 48:443 (1970), which is hereby incorporated by reference in its entirety; the search-for-similarity-method of Pearson and Lipman, Proc. Natl. Acad. Sci. USA, 85:2444 (1988), which is hereby incorporated by reference in its entirety; the algorithm of Karlin and Altschul, Proc. Natl. Acad. Sci. USA, 87:2264 (1990), which is hereby incorporated by reference in its entirety; modified as in Karhn and Altschul, i Proc. Natl. Acad. Sci. USA, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., Gene, 73:237 (1988), Higgins et al., CABIOS, 5:151 (1989); Corpet et al., Nucl. Acids Res., 16:10881 (1988); Huang et al, CABIOS, 8:155 (1992); and Pearson et al., Meth. Mol. Biol., 24:307 (1994), which are hereby incorporated by reference in their entirety. The ALIGN program is based on the algorithm of Myers and Miller, supra. The BLAST programs of Altschul et al., JMB, 215:403 (1990); Nucl. Acids Res., 25:3389 (1990), which are hereby incorporated by reference in their entirety, are based on the algorithm of Karlin and Altschul supra.

Software for performing BLAST analyses is publicly available through the National Center for Biotechnology Information and is accessible through its website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., Nucleic Acids Res. 25:3389 (1997), which is hereby incorporated by reference in its entirety. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E)

of 10, and the BLOSUM62 scoring matrix. See http://www.ncbi.nlm.nih.gov. Alignment may also be performed manually by inspection.

For purposes of the present invention, comparison of nucleotide sequences for determination of percent sequence identity to the sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and, therefore, do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. (e)(i) The term "substantial identity" of polynucleotide sequences means that a polynucleotide includes a sequence that has at least 51%, 52%, 53%, 54%, 55%, 56%, 57%, 58%, 59%, 60%, 61%, 62%, 63%, 64%, 65%, 66%, 67%, 68%, or 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267 (1984), which is hereby incorporated by reference in its entirety; $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, Part I Chapter 2 "Overview of Principles of Hybridization and the Strategy of Nucleic Acid Probe Assays," Elsevier, N.Y. (1993), which is hereby incorporated by reference in its entirety. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g. more than 100 nucleotides, is 4–6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC =3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Thus, the present invention, for example, may be directed to nucleic acid sequences that specifically hybridize to, or are substantially identical to, nucleic acid sequences that include any one of SEQ ID NOs 1–15.

Trimers and DNA Assemblies

As is described herein, a "trimer" is a structure formed by the association of three polynucleotides (see Example 1 and FIG. 8). The terms "trimer" and "Y-DNA" are used interchangably herein. The trimer is a generally Y-shaped structure having three branches. A "branch" is a structure formed by the association, for example, the hybridization, of portions of two polynucleotides. Each branch may have a sticky end. A sticky end is a single-stranded overhang portion of one of the polynucleotides forming the branch. In some embodiments of the present invention, the sticky ends can be 4, 5, 6, 7, 8, 9, or 10 nucleotides. The sticky end in some embodiments is a four nucleotide sticky end. In some embodiments, the sticky end includes, or is, TGAC (SEQ ID NO:16), GTCA (SEQ ID NO:17), CGAT (SEQ ID NO:18), ATCG (SEQ ID NO:19), GCAT (SEQ ID NO:20), ATGC (SEQ ID NO:21), TTGC (SEQ ID NO:22), GCAA (SEQ ID NO:23), or GGAT (SEQ ID NO:24). Sticky ends are designed so that the sticky ends of polynucleotides in different trimers will hybridize together. The trimers are to be ligated together. In one embodiment, SEQ ID NOs 1, 6, and 11 are combined to form a trimer. In another embodiment, SEQ ID NOs 2, 7, and 12 are combined to form a trimer. In another embodiment, SEQ ID NOs 3, 8, and 13 are combined to form a trimer. In another embodiment, SEQ ID NOs 4, 9, and 14 are combined to form a trimer. In another embodiment, SEQ ID NOs 5, 10, and 15 are combined to form a trimer. See FIG. 8.

A "DNA assembly" is a structure including at least two trimers associated together (see Example 2). The DNA assembly can be formed by hybridization of the sticky ends of at least 2 trimers, and the trimers may be ligated together. In some embodiments of the present invention, the assembly is isotropic, and in some embodiments, the assembly is anisotropic, thereby providing the ability to link other chemical entities. The terms "anneal" and "hybridize" are used interchangably herein and refer to the specific association of complementary strands of polynucleotides, for example, the specific association of complementary strands of DNA. The term "ligation" refers to the process of joining DNA molecules together with covalent bonds. For example, DNA ligation involves creating a phosphodiester bond between the 3' hydroxyl of one nucleotide and the 5' phosphate of another.

A DNA assembly may be synthesized following a divergent strategy (growing outwardly from an inner core trimer). A DNA assembly may be synthesized following a convergent strategy (growing inwardly from the outside).

Figure 4A:
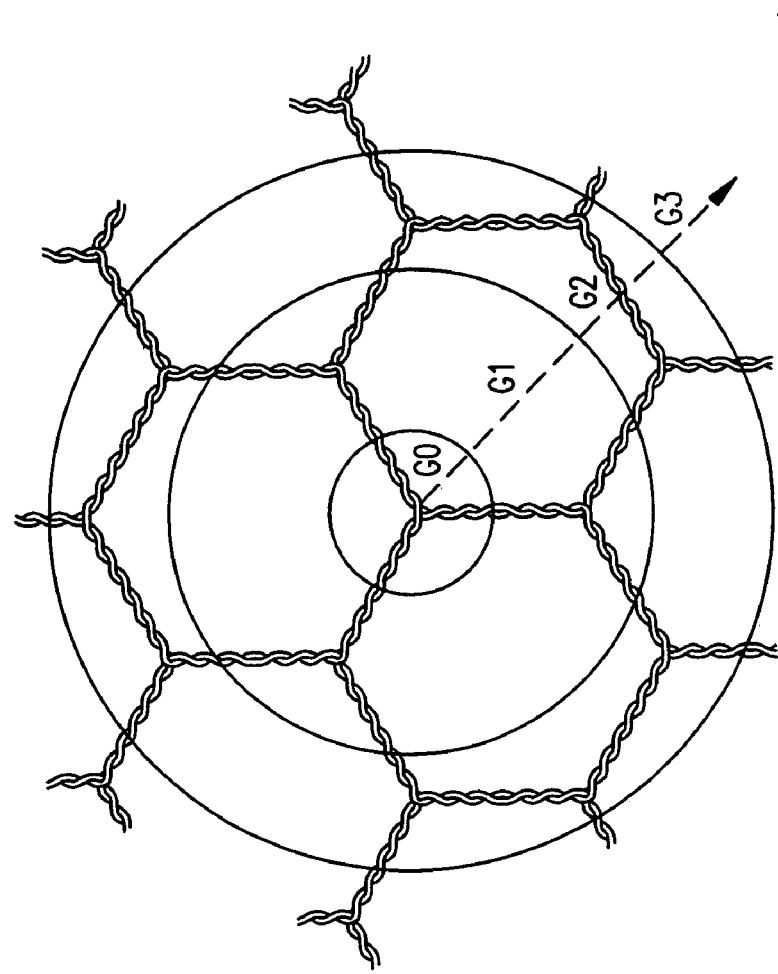
FIG. 4A is a schematic drawings of $G_2$ DL-DNA (left) and other higher generation DL-DNA (right).
Figure 4A:
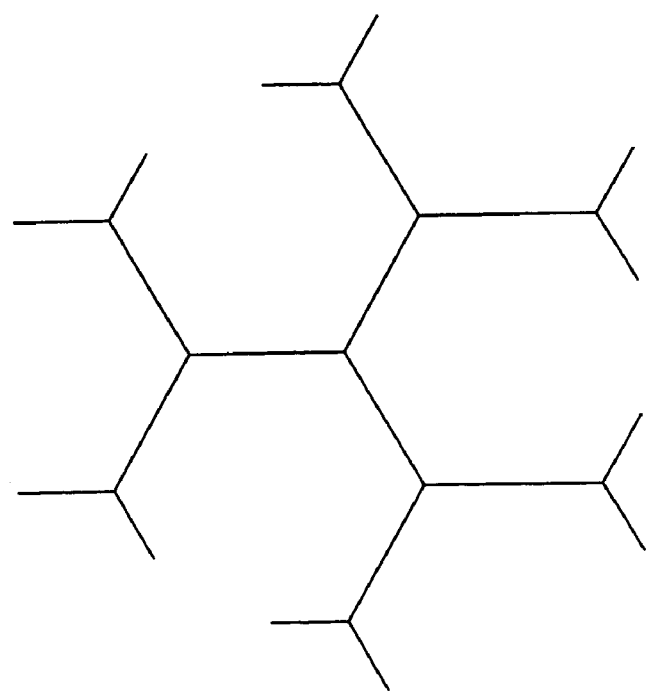
Figure 4B:
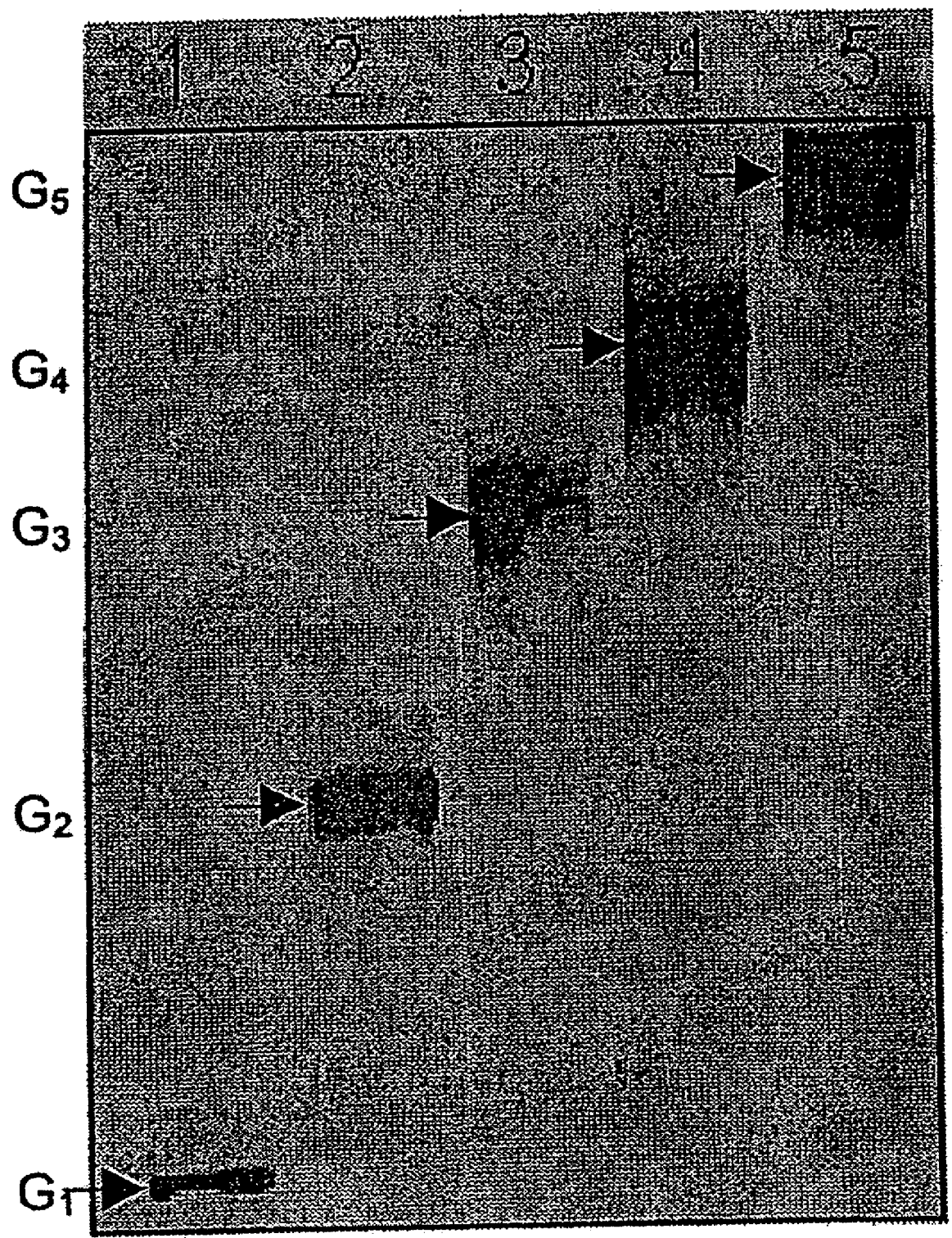
FIG. 4B depicts an evaluation of higher generation DL-DNA formation. Lanes 1, 2, 3, 4 and 5 correspond to $G_1$ DL-DNA, $G_2$ DL-DNA, $G_3$ DL-DNA, $G_4$ DL-DNA and $G_5$ DL-DNA, respectively.

The trimers of the present invention may be associated together to form DNA assemblies of different shapes. For example, two trimers may be associated together to form a DNA assembly with a "dumbbell" shape. "Dendrimer-like DNA" (DL-DNA) is a DNA assembly. A "honeycomb" structure is a repeating pattern of generally hexagonal structures formed by the association of trimers (see FIG. 1D and FIG. 4A (right hand portion) for an example of a honeycomb structure). The DNA assembly may also be in the form of a generally linear assembly of trimers.

The terms "nucleic acid sequence", "polynucleotide", and "oligonucleotide" are used interchangably herein.

It should be noted that the indefinite articles "a" and "an" and the definite article "the" are used in the present application, as is common in patent applications, to mean one or more unless the context clearly dictates otherwise.

EXAMPLES

Example 1

Design and Construction of Y-DNA

The sequences of the strands, shown in Table 1, were designed according to the standards set by Seeman (Seeman, *J Biomol Struct Dyn* 8:573–81 (1990), which is hereby incorporated by reference in its entirety) and commercially synthesized (Integrated DNA Technologies, Coralville, Iowa). All oligonucleotides were dissolved in annealing buffer (10 mM Tris, pH8.0, 50 mM NaCl, 1 mM EDTA) with a final concentration of 0.1 mM.

Y-shaped DNA (Y-DNA) were synthesized by mixing equal amounts of three oligonucleotide strands. The nomenclature is as follows: $Y_{0a}$, $Y_{0b}$, and $Y_{0c}$ are the three corresponding single oligonucleotide chains that form a $Y_0$-DNA ($Y_0$). Similarly, $Y_{1a}$, $Y_{1b}$, and $Y_{1c}$ are the three corresponding single oligonucleotide chains that form a $Y_1$-DNA ($Y_1$); and $Y_{na}$, $Y_{nb}$, and $Y_{nc}$ are the three corresponding single oligonucleotide chains that form a $Y_n$-DNA ($Y_n$). The reactions are the following: $Y_{0a}+Y_{0b}+Y_{0c}\rightarrow Y_0$, $Y_{1a}+Y_{1b}+Y_{1c}\rightarrow Y_1$, and $Y_{na}+Y_{nb}+Y_{nc}\rightarrow Y_n$, etc. (see FIG. 1A). All the mixtures were first incubated at 95° C. for 2 min, then quickly cooled to 60° C., and finally slowly cooled to 4° C.

Annealing Program:

|  | Control Lid | block 105 ° C. |
| --- | --- | --- |
| (Denaturation) | 95° C. | 2 min |
| (Cooling) | 65° C. | 2 min |
| (Annealing) | 60° C. | 5 min |
| (Annealing) | 60° C. | 0.5 min |
|  | Temperature increment −1° C. | |
| (number of cycle) | go to (5) Rep 40 | |
| (Hold) | 4° C. | enter |

Figure 2A:
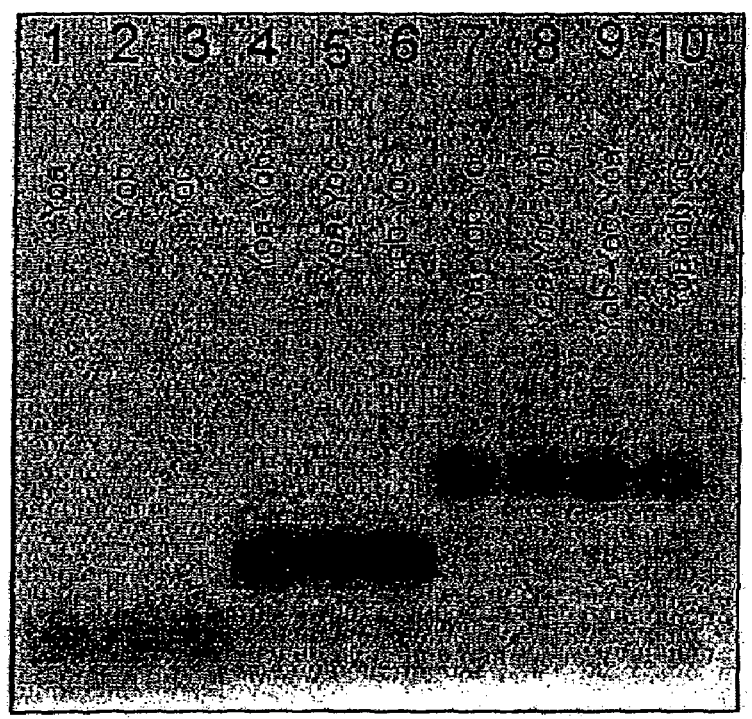
FIG. 2A depicts an evaluation of $Y_0$-DNA by argarose gel. Lanes 1, 2 and 3 are oligonucleotides $Y_{0a}$, $Y_{0b}$, $Y_{0c}$, respectively. Lanes 4, 5 and 6 correspond to the annealing products of ($Y_{0a}$ and $Y_{0b}$), ($Y_{0a}$ and $Y_{0c}$), and ($Y_{0b}$ and $Y_{0c}$), respectively. Lanes 7, 8 and 9 correspond to the stepwise annealing products of ($Y_{0a}$, $Y_{0b}$ and $Y_{0c}$), ($Y_{0a}$, $Y_{0c}$ and $Y_{0b}$), and ($Y_{0b}$, $Y_{0c}$ and $Y_{0a}$), respectively. Lane 10 corresponds to the one-pot annealing product of ($Y_{0a}$, $Y_{0b}$ and $Y_{0c}$).
Figure 2B:
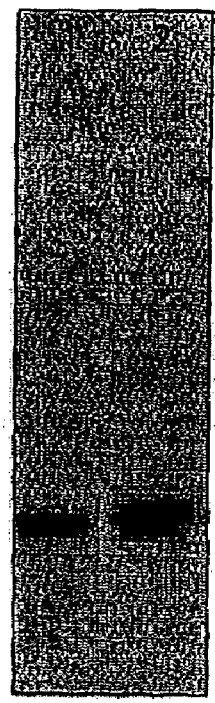
FIG. 2B depicts an evaluation of Y-DNA stability. Lane 1 represents freshly made Y-DNA and lane 2 represents the same Y-DNA stored at 4° C. for 30 days.
Figure 3B:
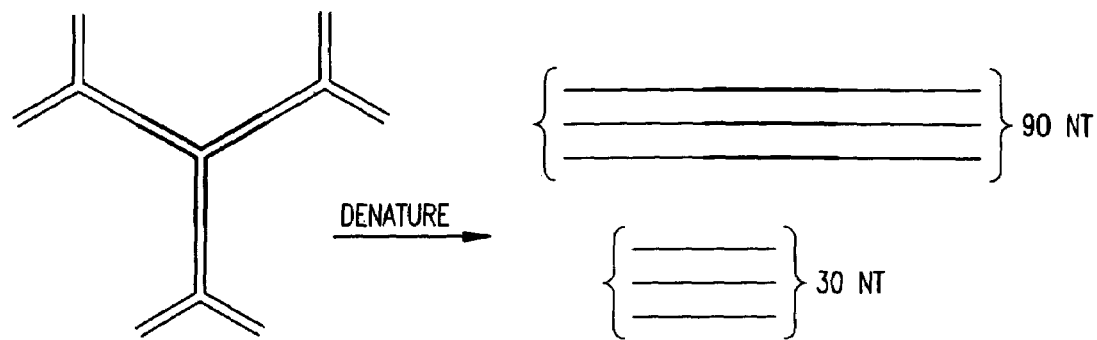
FIG. 3B is a schematic drawing of the denaturation strategy used to confirm the $G_1$ DL-DNA structure. After $G_1$ DL-DNA denaturation, six oligonucleotides were generated; three of these six oligonucleotides were new species with a unique length (90 bases). The remaining three were 30 bases.
Figure 3C:
In FIG. 3C, lane 1 is Y-DNA and lane 2 is $G_1$ DL-DNA.
Figure 3D:
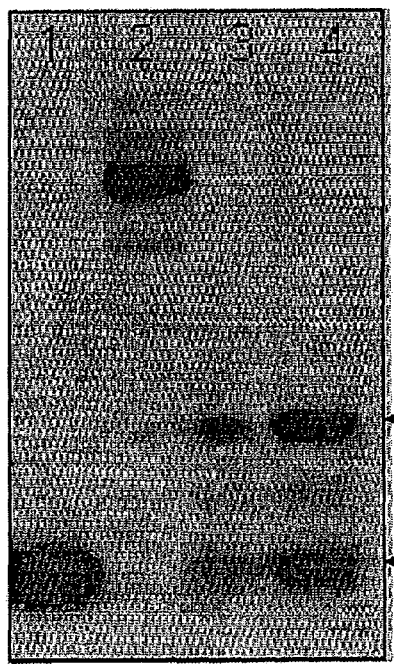
In FIG. 3D, lane 1 is a molecular marker (oligonucleotide $Y_{0a}$). Lane 2 is $G_1$ DL-DNA without denaturing. Lanes 3 and 4 correspond to 0.25 μg and 0.5 μg of the denatured $G_1$ DL-DNA, respectively.
Figure 3E:
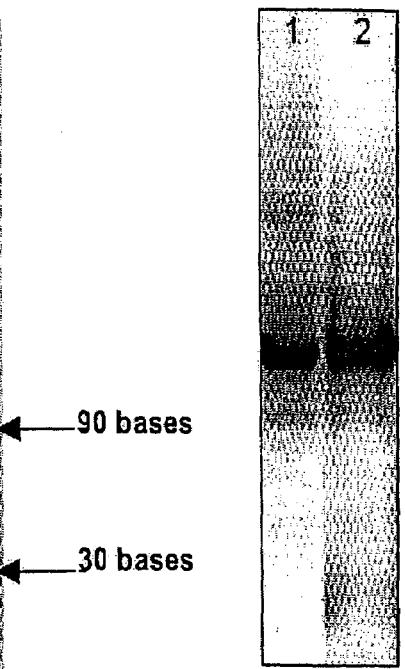
FIG. 3E presents an evaluation of $G_1$ DL-DNA stability. $G_1$ on Lane 1 was freshly made. $G_1$ on Lane 2 was the same as that on Lane 1 but was stored for 45 days before gel electrophoresis.

Y-DNAs are the basic building blocks for the DL-DNA. Two strategies were adopted to synthesize the Y-DNA: stepwise and all-in-one. In the stepwise approach (FIG. 1A), two oligonucleotides with complementary regions formed one arm of a Y-DNA; then a third oligonucleotide, that was complementary to the first two un-matched regions of oligonucleotides, formed the other two arms of the Y-DNA. In the all-in-one approach, all three oligonucleotides were mixed together in equal amounts to form the Y-DNA. In both cases, high-resolution gel electrophoresis was applied to evaluate the formation of Y-DNA (FIG. 2).

Nucleic acid samples were evaluated on either 3% agarose ready gel (Bio-Rad, Hercules, Calif.) or 4–20% TBE polyacrylamide ready gel (Bio-Rad) at 100 volts. In some cases, in order to confirm a particular structure, single stranded DNA were obtained by denaturing where NaOH was added to the nucleic acid samples to a final concentration of 20 mM. The alkalized samples were then incubated at 95° C. for 2 min and cooled immediately on ice before electrophoresis.

The electrophoretic mobility of an oligonucleotide depends on its size, shape and extent of base pairing (Kallenbach et al., *J Biomol Struct Dyn* 1, 159–68 (1983), which is hereby incorporated by reference in its entirety). Lanes 1–3 of FIG. 2 show the individual single DNA strands (30-mers): $Y_{0a}$, $Y_{0b}$, and $Y_{0c}$. Lanes 4–6 of FIG. 2 represent three possible combinations of $Y_{0a}$, $Y_{0b}$, and $Y_{0c}$, i.e. $Y_{0a}$ with $Y_{0b}$, $Y_{0a}$ with $Y_{0c}$, and $Y_{0b}$ with $Y_{0c}$. One major band appears on the gel, and the mobility is less than the single DNA strands, indicating that one arm of Y-DNA has been formed. Lanes 7–9 of FIG. 2 show the stepwise equal molar mixtures of all three strands, and lane 10 of FIG. 2 shows the all-in-one equal molar mixtures of all three strands. There is no difference in results between stepwise and all-in-one synthesis. Dominant bands, where the mobility has been retarded, suggest that Y-DNA was formed as predicted (See FIG.1A). The estimated yield of Y-DNA is more than 90%. Other Y-DNA, $Y_1$, $Y_2$, $Y_3$, and $Y_4$, were similarly built.

Example 2

Design, Construction, and Evaluation of Dendrimer-Like DNA

Figure 1B:
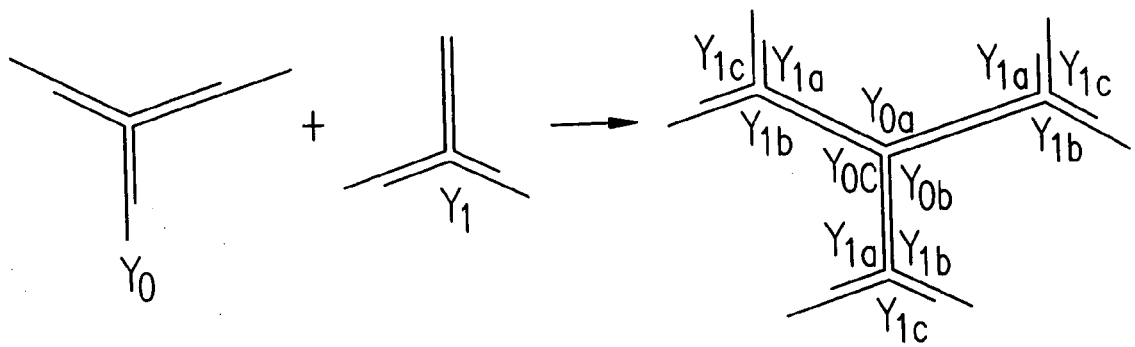
FIG. 1B depicts the assembly of first generation dendrimer-like DNA ($G_1$). The core $Y_0$-DNA was ligated with three "$Y_1$"s, all with specifically designed sticky ends. The ligation was unidirectional.
Figure 1C:
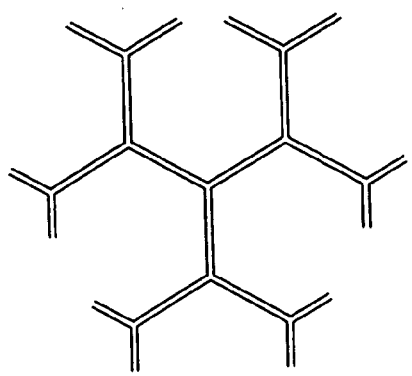
FIG. 1C depicts the assembly of second generation dendrimer-like DNA ($G_2$). $G_1$ DNA was ligated with six $Y_2$-DNAs.
Figure 1D:
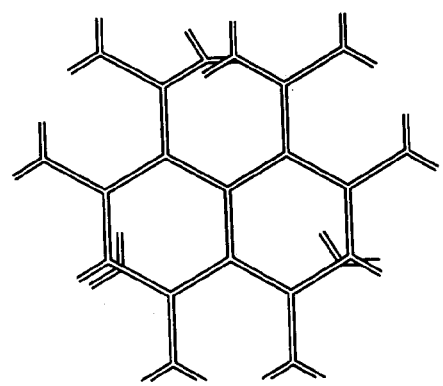
FIG. 1D depicts the assembly of third generation dendrimer-like DNA ($G_3$) and $G_4$.

For constructing DL-DNA, individual Y-DNAs were ligated specifically to other Y-DNAs, without self-ligation. The ligations were performed with Fast-Link DNA Ligase (Epicentre Technologies, Madison, Mich.). T4 DNA ligase may also be used (Promega Corporation, Madison, Wis.). The reaction scheme is shown in FIG. 1B and 1C. The nomenclature of DL-DNA is as follows: the core of the dendrimer, $Y_0$, is designated as $G_0$, the 0 generation of DL-DNA. After $Y_0$ is ligated with $Y_1$, the dendrimer is termed the $1^{st}$ generation of DL-DNA ($G_1$), and so on. The $n^{th}$ generation of DL-DNA is noted as $G_n$.

As noted above, each Y-DNA is composed of three single DNA strands (Table 1). These strands are designed so that ligations between $Y_i$ and $Y_j$ can only occur when $i\neq j$ (no self-ligation). In addition, the ligation can only occur in one direction, that is, $Y_0\rightarrow Y_1\rightarrow Y_2\rightarrow Y_3\rightarrow Y_4$. In other words, when $Y_0$ is ligated to $Y_1$, with 1:3 stoichiometry, three $Y_1$, units are linked with one $Y_0$ forming $1^{st}$ generation of DL-DNA ($G_1$). $G_1$ can then be ligated to six $Y_2$ units due to the fact that there are 6 arms of $Y_1$, now (each $Y_1$, posses two arms), and the resulting product is a second-generation DL-DNA ($G_2$). A third ($G_3$), fourth ($G_4$), and even higher generation DL-DNA could be synthesized in a similar way. Notice that the resulting dendrimers ($G_n$) have only one possible conformation due to the designed unidirectional ligations. The general format on the $n^{th}$ generation DL-DNA is $G_n=(Y_0)(3Y_1)(6Y_2) \ldots (3\times 2^{n-1}Y_n)$, where n is the generation number and $Y_n$ is the $n^{th}$ Y-DNA. The total number of Y-DNA in an $n^{th}$ generation DL-DNA are $3\times 2^{n-1}-2$. Therefore, the growth of DL-DNA from $n^{th}$ generation to $(n+1)^{th}$ generation requires a total of $3\times 2^n$ new $Y_{n+1}$-DNA.

The first generation DL-DNA was built by ligating $Y_0$ and $Y_1$ with 1:3 stoichiometry. The ligation product migrates as a single band, and its mobility is slower than that of its building block, $Y_0$. The presence of a single band indicates that a new molecular species with a well-defined stoichiometry has formed. The estimated yield is more than 95%.

To further evaluate the structure of the ligation product, it was denatured and examined by gel electrophoresis. There are two major bands for the denatured sample one with the same mobility as the single strand DNA $Y_{0a}$ (30-mer) and one with slower mobility (see arrow, a single stranded 90-mer strand), which is exactly what one would expect according to the assembly scheme. Notice that denaturing $G_1$ DL-DNA results in two sizes of single strands left: one 30-mer ($Y_{1b}$) and the other 90-mer (($Y_{1a}$)($Y_{0a}$)($Y_{1c}$), ($Y_{1a}$)($Y_{0b}$)($Y_{1c}$), and ($Y_{1a}$)($Y_{0c}$)($Y_{1c}$)). Taken together, these results indicate that the formation of the $1^{st}$ generation of DL-DL-DNA is as expected with high yield.

The second, third, and fourth generation DL-DNA were synthesized with the stepwise approach and evaluated by gel electrophoresis. With each increased generation, the mobility of the ligated product decreased as predicted. The yield and the purity of higher generations ($G_3$ and $G_4$) DL-DNA did not decrease, even without purification, indicating that the stepwise synthesis approach is very robust.

Example 3

Atomic Force Imaging of DL-DNA

A 5 μl DNA sample was placed onto the surface of freshly cleaved mica (Ted Pella, Redding, Calif.) functionalized with aminopropyltriethoxysilane (APTES, Aldrich) and allowed to adsorb to the mica surface for approximately 20 minutes. The mica was then rinsed in Milli-Q water and dried with compressed air. Images were taken in air using Tapping mode on a Dimensions 3100 Atomic Force Microscope (Digital Instruments, Santa Barbarra, Calif.), and the amplitude setpoint was adjusted to maximize resolution while minimizing the force on the sample. Briefly, the amplitude setpoint was increased until the tip disengaged the surface, and then decreased by 0.1 to 0.2 volts such that the tip was engaged and applying the minimal force onto the sample surface. Images were processed with a flattening filter.

Figure 5:
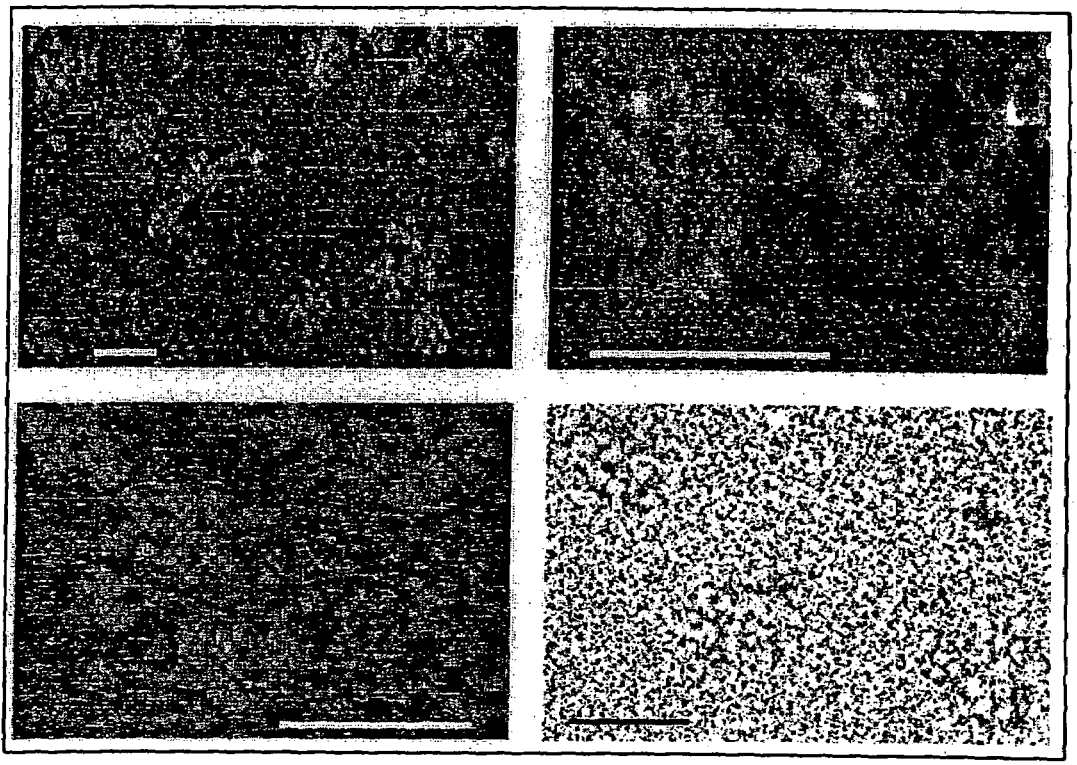
FIG. 5 presents images of DL-DNA: AFM images of $G_4$ DL-DNA on mica surface using standard silicon tip (lower left) and single walled carbon nanotube (SWNT) tip (top left and right), and TEM image of $G_4$ DL-DNA (lower right). Scale bars correspond to 100 nm.
Figure 6:
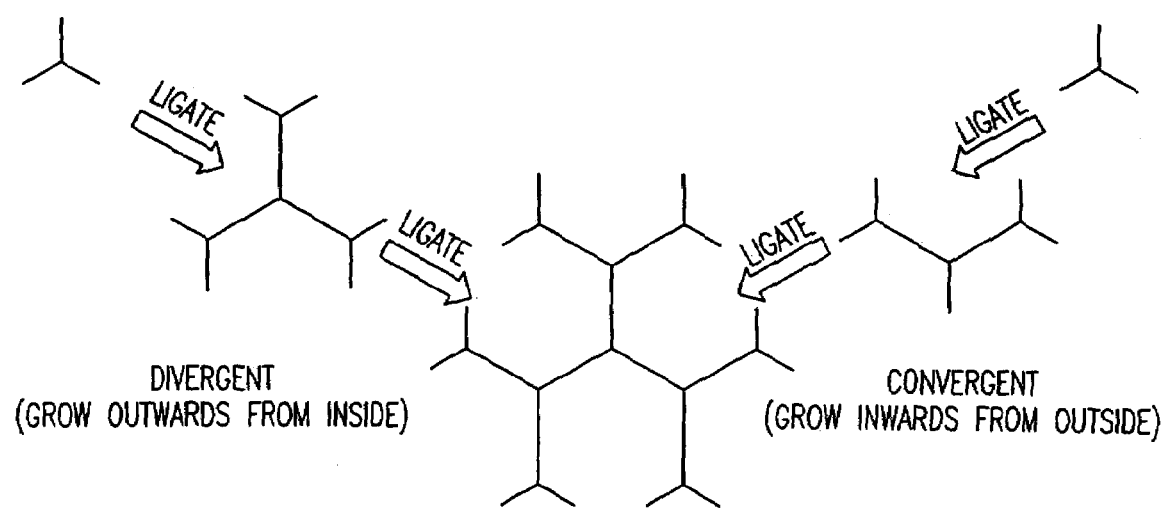
FIG. 6 depicts divergent and convergent synthesis of a nucleic acid assembly.
Figure 7:
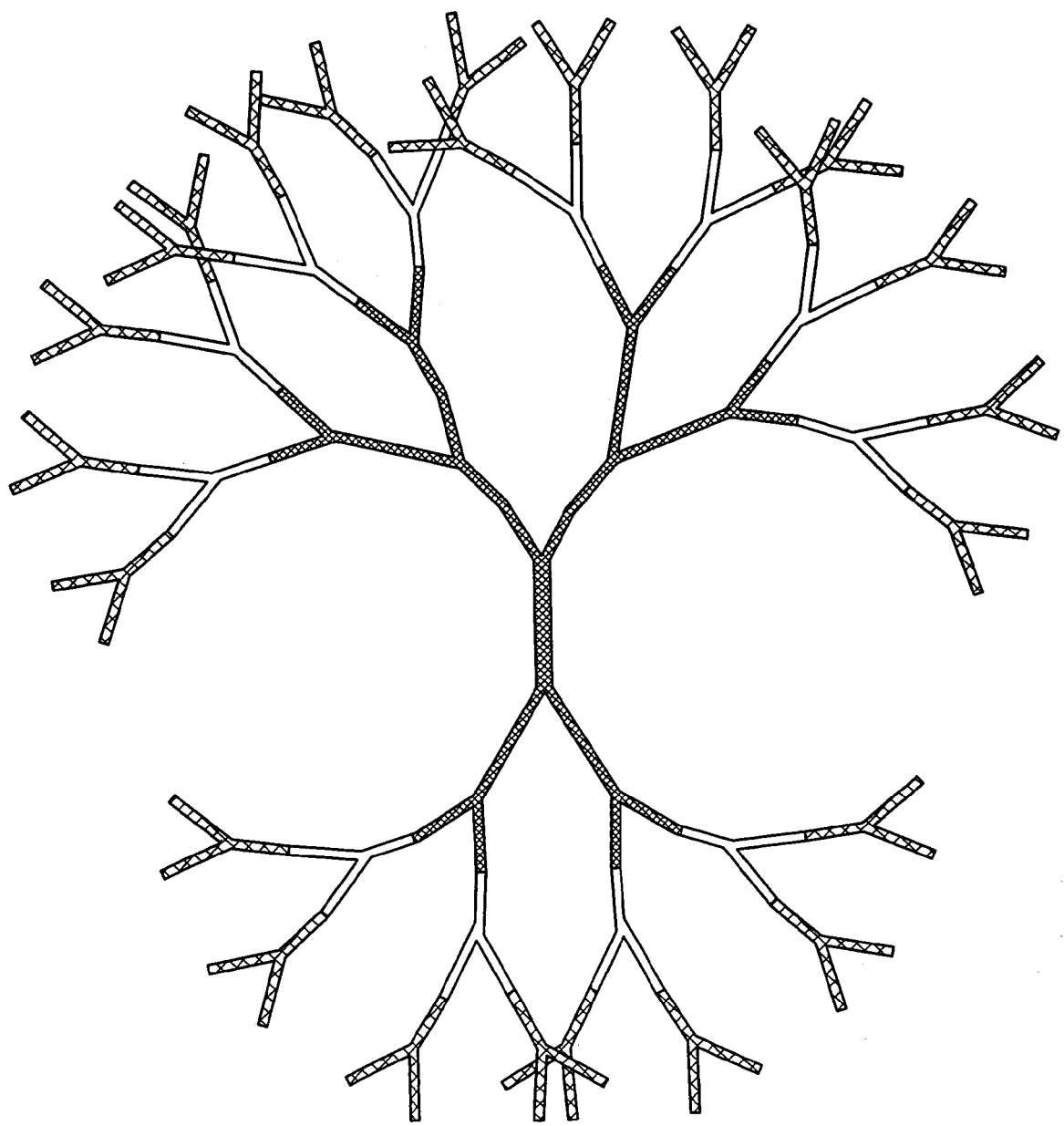
FIG. 7 depicts dendrimer-like DNA.

As noted by high-resolution agarose gel electrophoresis, different generations of dendrimers were assembled from basic Y-DNA building blocks. To confirm that the gel-shifted species were indeed DL-DNA molecules, the $4_{th}$ generation DL-DNA was examined by AFM. FIG. 5 shows clusters of nanoparticles with highly branched DL-DNA molecules. The width of DNA strands was measured to be approximately 9.0 nm, consistent with the radius of curvature of the AFM tips. The measured diameter of $4^{th}$ generation of DL-DNA nanostructure was 71.2±6.7 nm, which was very close to the theoretically calculated value (69.0 nm) considering the relative flexibility of DNA molecules.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed:

1. A method of making a three-dimensional nucleic acid structure formed with a trimer comprising:
   combining a first, a second, and a third polynucleotide in a solution, wherein at least a portion of the first polynucleotide is complementary to at least a portion of the second polynucleotide, wherein at least a portion of the first polynucleotide is complementary to at least a portion of the third polynucleotide; and wherein at least a portion of the second polynucleotide is complementary to at least a portion of the third polynucleotide; and
   maintaining the solution at conditions effective for the first, second, and third polynucleotides to associate together to form a trimer, wherein each polynucleotide comprises a sticky end, wherein the sequence of each sticky end is non-complementary.

2. The method of claim 1, wherein said combining comprises the steps of:
   combining the first polynucleotide with the second polynucleotide in a solution to form a mixture; and
   subsequently combining the third polynucleotide with the first and second polynucleotides in the solution.

3. The method of claim 1, wherein each polynucleotide comprises a first region, a second region located 3' to the first region, and a third region located 3' to the second region, wherein the second region of the first polynucleotide comprises a region complementary to the third region of the third polynucleotide, the third region of the first polynucleotide comprises a region complementary to the second region of the second polynucleotide, the third region of the second polynucleotide comprises a region complementary to the second region of the third polynucleotide.

4. The method of claim 3, wherein the first region of the first, second, and third polynucleotides comprises the sticky end.

5. The method of claim 1, wherein the first, second, and third polynucleotides are DNA.

6. The method of claim 1, wherein the structure is a dendrimer structure.

7. The method of claim 1, wherein the structure is anisotropic.

8. The method of claim 1, wherein the structure is isotropic.

9. The method of claim 1, wherein the structure is a second generation ligation product of a plurality of the trimers.

10. The method of claim 1, wherein the structure is a third generation ligation product of a plurality of the trimers.

11. The method of claim 1, wherein the structure is a fourth generation ligation product of a plurality of the trimers.

12. The method of claim 1, wherein each of the sticky ends comprised on said trimer is comprised of a different polynucleotide sequence.

13. The method of claim 1, wherein the association is of a plurality of the trimers in an all-in-one reaction.

14. The method of claim 1, wherein the at least two sticky ends are non-palindromic.

* * * * *

SEQUENCE LISTING

```
<160> NUMBER OF SEQ ID NOS: 30

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:  probe

<400> SEQUENCE: 1
tgactggatc cgcatgacat tcgccgtaag                                    30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:  probe

<400> SEQUENCE: 2
gtcatggatc cgcatgacat tcgccgtaag                                    30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:  probe

<400> SEQUENCE: 3
atcgtggatc cgcatgacat tcgccgtaag                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:  probe

<400> SEQUENCE: 4
atgctggatc cgcatgacat tcgccgtaag                                    30

<210> SEQ ID NO 5
```

```
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 5
gcaatggatc cgcatgacat tcgccgtaag                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 6
tgaccttacg gcgaatgacc gaatcagcct                                    30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 7
cgatcttacg gcgaatgacc gaatcagcct                                    30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 8
gcatcttacg gcgaatgacc gaatcagcct                                    30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 9
ttgccttacg gcgaatgacc gaatcagcct                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 10
ggatcttacg gcgaatgacc gaatcagcct                                    30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 11
```

```
tgacaggctg attcggttca tgcggatcca                                30
```

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 12

```
cgataggctg attcggttca tgcggatcca                                30
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 13

```
gcataggctg attcggttca tgcggatcca                                30
```

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 14

```
ttgcaggctg attcggttca tgcggatcca                                30
```

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: probe

<400> SEQUENCE: 15

```
ggataggctg attcggttca tgcggatcca                                30
```

<210> SEQ ID NO 16
<211> LENGTH: 4
<212> TYPE: DNA
<213> ORGANISM: Artificial Sequence
<220> FEATURE:
<223> OTHER INFORMATION: Description of Artificial Sequence: probe

<400> SEQUENCE: 16

```
tgac                                                             4
```

<210> SEQ ID NO 17
<211> LENGTH: 4
<212> TYPE: DNA
<213> ORGANISM: Artificial Sequence
<220> FEATURE:
<223> OTHER INFORMATION: Description of Artificial Sequence: probe

<400> SEQUENCE: 17

```
gtca                                                             4
```

<210> SEQ ID NO 18
<211> LENGTH: 4
<212> TYPE: DNA

```
<213> ORGANISM: Artificial Sequence
<220> FEATURE:
<223> OTHER INFORMATION: Description of Artificial Sequence: probe

<400> SEQUENCE: 18 cgat                                                                4

<210> SEQ ID NO 19
<211> LENGTH: 4
<212> TYPE: DNA
<213> ORGANISM: Artificial Sequence
<220> FEATURE:
<223> OTHER INFORMATION: Description of Artificial Sequence: probe

<400> SEQUENCE: 19 atcg                                                                4

<210> SEQ ID NO 20
<211> LENGTH: 4
<212> TYPE: DNA
<213> ORGANISM: Artificial Sequence
<220> FEATURE:
<223> OTHER INFORMATION: Description of Artificial Sequence: probe

<400> SEQUENCE: 20 gcat                                                                4

<210> SEQ ID NO 21
<211> LENGTH: 4
<212> TYPE: DNA
<213> ORGANISM: Artificial Sequence
<220> FEATURE:
<223> OTHER INFORMATION: Description of Artificial Sequence: probe

<400> SEQUENCE: 21 atgc                                                                4

<210> SEQ ID NO 22
<211> LENGTH: 4
<212> TYPE: DNA
<213> ORGANISM: Artificial Sequence
<220> FEATURE:
<223> OTHER INFORMATION: Description of Artificial Sequence: probe

<400> SEQUENCE: 22 ttgc                                                                4

<210> SEQ ID NO 23
<211> LENGTH: 4
<212> TYPE: DNA
<213> ORGANISM: Artificial Sequence
<220> FEATURE:
<223> OTHER INFORMATION: Description of Artificial Sequence: probe

<400> SEQUENCE: 23 gcaa                                                                4

<210> SEQ ID NO 24
<211> LENGTH: 4
<212> TYPE: DNA
<213> ORGANISM: Artificial Sequence
<220> FEATURE:
<223> OTHER INFORMATION: Description of Artificial Sequence: probe

<400> SEQUENCE: 24 ggat                                                                4
```

-continued

```
<210> SEQ ID NO 25
<211> LENGTH: 13
<212> TYPE: DNA
<213> ORGANISM: Artificial Sequence
<220> FEATURE:
<223> OTHER INFORMATION: Description of Artificial Sequence: probe

<400> SEQUENCE: 25
tggatccgca tga                                                              13

<210> SEQ ID NO 26
<211> LENGTH: 13
<212> TYPE: DNA
<213> ORGANISM: Artificial Sequence
<220> FEATURE:
<223> OTHER INFORMATION: Description of Artificial Sequence: probe

<400> SEQUENCE: 26
cattcgccgt aag                                                              13

<210> SEQ ID NO 27
<211> LENGTH: 13
<212> TYPE: DNA
<213> ORGANISM: Artificial Sequence
<220> FEATURE:
<223> OTHER INFORMATION: Description of Artificial Sequence: probe

<400> SEQUENCE: 27
cttacggcga atg                                                              13

<210> SEQ ID NO 28
<211> LENGTH: 13
<212> TYPE: DNA
<213> ORGANISM: Artificial Sequence
<220> FEATURE:
<223> OTHER INFORMATION: Description of Artificial Sequence: probe

<400> SEQUENCE: 28
accgaatcag cct                                                              13

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: probe

<400> SEQUENCE: 29
aggctgattc ggt                                                              13

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: probe

<400> SEQUENCE: 30
tcatgcggat cca                                                              13
```